(12) United States Patent
Licisyn

(10) Patent No.: US 11,690,926 B2
(45) Date of Patent: Jul. 4, 2023

(54) STERILIZING APPARATUS FOR INPUT DEVICES OF COMPUTERS

(71) Applicant: Thomas A. Licisyn, Charlotte, NC (US)

(72) Inventor: Thomas A. Licisyn, Charlotte, NC (US)

(*) Notice: Subject to any disclaimer, the term of this patent is extended or adjusted under 35 U.S.C. 154(b) by 310 days.

(21) Appl. No.: 17/131,321

(22) Filed: Dec. 22, 2020

(65) Prior Publication Data

US 2022/0193293 A1 Jun. 23, 2022

(51) Int. Cl.
*A61L 2/24* (2006.01)
*A61L 2/10* (2006.01)
*A47B 88/46* (2017.01)
*A47B 88/47* (2017.01)

(52) U.S. Cl.
CPC .............. *A61L 2/24* (2013.01); *A47B 88/46* (2017.01); *A47B 88/47* (2017.01); *A61L 2/10* (2013.01); *A61L 2202/11* (2013.01); *A61L 2202/121* (2013.01); *A61L 2202/122* (2013.01); *A61L 2202/14* (2013.01)

(58) Field of Classification Search
CPC .......... A61L 2/24; A61L 2/10; A61L 2202/11; A61L 2202/121; A61L 2202/122; A61L 2202/14; A47B 88/47; A47B 88/46
USPC ........................... 250/453.11, 454.11, 455.11
See application file for complete search history.

(56) References Cited

U.S. PATENT DOCUMENTS

| | | | |
|---|---|---|---|
| 6,278,122 B1 | 8/2001 | Gagnon | |
| 6,458,331 B1 | 10/2002 | Roberts | |
| 7,372,044 B2 | 5/2008 | Ross | |
| 7,692,159 B2 | 4/2010 | Lane | |
| 8,084,752 B2 | 12/2011 | Ranta | |
| 8,087,737 B2 | 1/2012 | Shoenfeld | |
| 10,413,625 B2 | 9/2019 | Pangan, Jr. et al. | |
| 11,116,857 B1* | 9/2021 | Benin | A61L 2/24 |
| 2020/0353111 A1* | 11/2020 | Schmiddem | A46B 17/065 |
| 2021/0139222 A1* | 5/2021 | Gisholt | B65D 25/04 |

* cited by examiner

*Primary Examiner* — Nicole M Ippolito
(74) *Attorney, Agent, or Firm* — Kanika Radhakrishnan; Evergreen Valley Law Group

(57) ABSTRACT

Embodiments of the present disclosure provide a sterilization apparatus. The sterilization apparatus includes a housing. A drawer is slidably secured to the housing and adapted to receive input devices. The drawer is configured to operate between a retracted position, an intermediate position and an extended position. A plurality of ultraviolet (UV) lights is mounted within the housing and configured to emit UV radiation for a pre-determined time for sterilizing the input devices. A closure member is movably coupled to the housing. The closure member is operated between an open position and a closed position by manually applying force on the closure member, thereby causing the closure member to be pushed down by a distance within the housing. The closure member pushed down within the housing collectively operates a hinge mechanism, a cam and lever mechanism and a rotary mechanism, thereby configuring the closure member to the open and position positions.

20 Claims, 12 Drawing Sheets

STERILIZING APPARATUS FOR INPUT DEVICES OF COMPUTERS

TECHNICAL FIELD

The present disclosure relates to a sterilizing apparatus for input devices and, more particularly relates, to an ultraviolet (UV) sterilizing apparatus for the input devices of computers, such as a keyboard and a mouse.

BACKGROUND

In the present scenario, people rely on computing devices (e.g., personal computer, laptop, and gaming device) for performing daily activities. The computing devices may include input devices, such as a mouse, a keyboard, or a touchscreen for receiving inputs from the people. As the input devices are often used by many people, they may be prone to the transmission of bacteria and germs from one person to another person. The transmission of bacteria and other pathogens may cause adverse health diseases to an individual. Therefore, the input devices are required to be sanitized after every use to prevent transmission of the bacteria and germs from one person to another person.

Typically, the input devices may be sanitized or cleaned by using liquid cleaners, such as disinfectant wipes or cleaning agents after every usage to prevent transmission of the bacteria and germs. However, cleaning the input devices with the liquid cleaners can damage the electronic equipment (i.e. the input devices). Also, the use of liquid cleans may lead to an electrical short circuit when the liquid cleaners sprayed onto the input devices come in contact with the conducting elements. Further, efficiency in sanitizing the input devices may vary based on the person engaged in cleaning the input devices. For example, the person cleaning the input device may only wipe a portion of the keyboard due to the inability to access all surfaces of the input devices which may be infected. The liquid disinfecting agents are also limited in their ability to access all the surfaces of the input devices which may be infected. This leads to incomplete sanitization of the input devices. The use of liquid disinfecting agents generates solid waste for disposal. The solid wastes from the liquid cleaners are environmentally unfriendly.

Therefore, there is a need for techniques to overcome one or more limitations stated above in addition to providing other technical advantages.

SUMMARY

Various embodiments of the present disclosure provide sterilizing apparatus for input devices.

In an embodiment, a sterilization apparatus is disclosed. The sterilization apparatus includes a housing. The housing at least includes a first sidewall and a second sidewall. A drawer is slidably secured to the housing via guide rails mounted to the first and second sidewalls. The drawer is adapted to receive input devices. The drawer is configured to operate between a retracted position, an intermediate position and an extended position. A rotary mechanism is secured to the first sidewall and positioned proximate to a distal portion of the housing. The rotary mechanism is operatively coupled to the drawer. The rotary mechanism is configured to lock and unlock the drawer, thereby operating the drawer between the retracted position, the intermediate position and the extended position. A plurality of ultraviolet (UV) lights is mounted within the housing. The plurality of UV lights is configured to emit UV radiation for a pre-determined time for sterilizing the input devices resting on the drawer. A closure member is movably coupled to the housing and positioned at an upper portion of the housing. The closure member is configured to operate between an open position and a closed position. A cam and lever mechanism is secured to the first sidewall and positioned proximate to a proximal portion of the housing. The cam and lever mechanism is operatively coupled to the closure member. A hinge mechanism is secured to the first sidewall and operatively coupled to the closure member. The hinge mechanism is configured to operate the closure member between the open position and the closed position. The closure member is operated between the open position and the closed position by manually applying force on the closure member, thereby causing the closure member to be pushed down by a distance within the housing. Pushing down of the closure member within the housing collectively operates the hinge mechanism and the cam and lever mechanism, thereby configuring the closure member to operate between the open position and the closed position.

In another embodiment, a sterilization apparatus for input devices is disclosed. The sterilization apparatus includes a housing at least includes a first sidewall and a second sidewall. A drawer is slidably secured to the housing via guide rails mounted to the first and second sidewalls. The drawer is adapted to receive the input devices. The drawer is configured to operate between a retracted position, an intermediate position and an extended position. A rotary mechanism is secured to the first sidewall and positioned proximate to a distal portion of the housing. The rotary mechanism is operatively coupled to the drawer. The rotary mechanism is configured to lock and unlock the drawer, thereby operating the drawer between the retracted position, the intermediate position and the extended position. A plurality of ultraviolet (UV) lights is mounted within the housing. The plurality of UV lights is configured to emit UV radiation for a pre-determined time for sterilizing the input devices resting on the drawer. A closure member is movably coupled to the housing and positioned at an upper portion of the housing. The closure member is configured to operate between an open position and a closed position. A cam and lever mechanism is secured to the first sidewall and positioned proximate to a proximal portion of the housing. The cam and lever mechanism is operatively coupled to the closure member. A hinge mechanism is secured to the first sidewall and operatively coupled to the closure member. The hinge mechanism is configured to operate the closure member between the open position and the closed position. The closure member is operated between the open position and the closed position by manually applying force on the closure member, thereby causing the closure member to be pushed down by a distance within the housing. Pushing down of the closure member within the housing collectively operates the hinge mechanism and the cam and lever mechanism, thereby configuring the closure member to operate between the open position and the closed position. The sterilization apparatus further includes one or more sensors communicably coupled to the closure member and the drawer. The one or more sensors are configured to detect and track the movement of the closure member operating in the open position and the closed position and the movement of the drawer operating in the retracted position, the intermediate position and the extended position. A timer circuit is communicably coupled to the one or more sensors. The timer circuit activates the plurality of UV lights for the pre-determined time to sterilize the input devices based on receiving sensory signals from the one or more sensors related to the drawer and the closure member operated in the retracted position and the closed position respectively.

BRIEF DESCRIPTION OF THE FIGURES

The following detailed description of illustrative embodiments is better understood when read in conjunction with the appended drawings. For the purpose of illustrating the present disclosure, exemplary constructions of the disclosure are shown in the drawings. However, the present disclosure is not limited to a specific device or a tool and instrumentalities disclosed herein. Moreover, those in the art will understand that the drawings are not to scale. Wherever possible, like elements have been indicated by identical numbers.

Figure 1A:
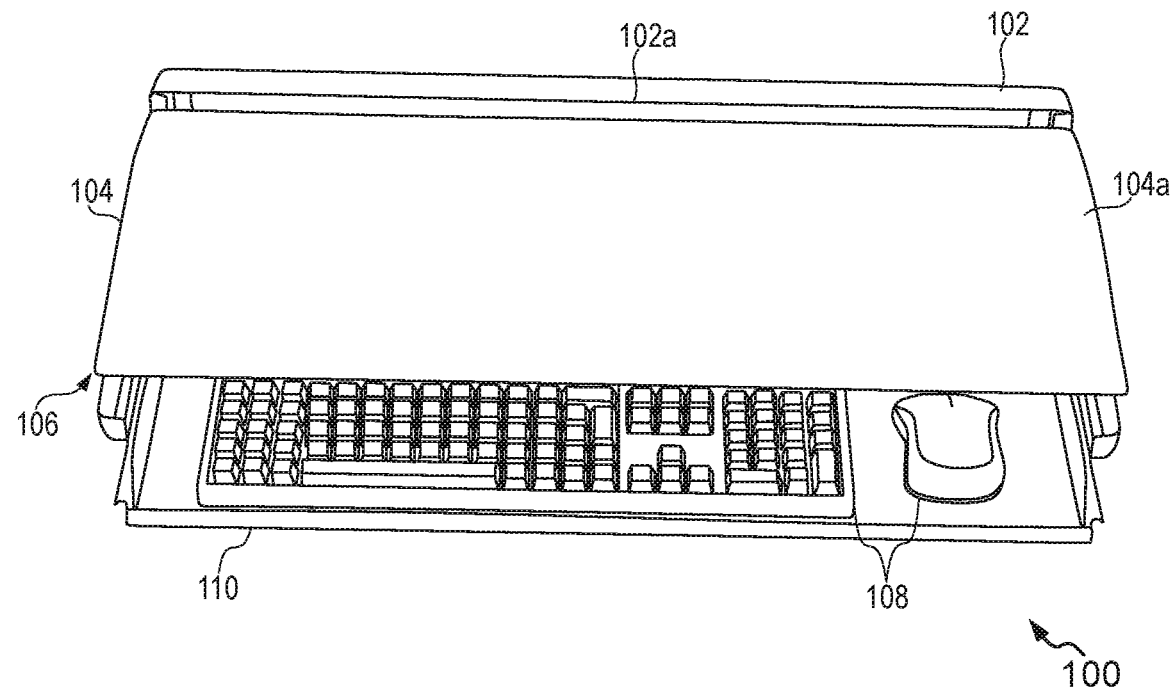
FIG. 1A illustrates a schematic view of a sterilizing apparatus operated in an intermediate position, in accordance with an example embodiment of the present disclosure.

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Reference in this specification to "one embodiment" or "an embodiment" means that a particular feature, structure, or characteristic described in connection with the embodiment is included in at least one embodiment of the present disclosure. The appearances of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

Overview

Various embodiments of the present disclosure provide a sterilization apparatus. In an embodiment, the sterilization apparatus includes a housing for encasing input devices such as, a keyboard and a mouse. A drawer is slidably secured to the housing via guide rails mounted to a first sidewall and a second sidewall of the housing. The drawer is adapted to receive the input devices. The drawer is configured to operate between a retracted position, an intermediate position and an extended position. The drawer is configured to assume the intermediate position from the retracted position due to force exerted by a first spring member on a rear portion of the drawer. A closure member is movably coupled to the housing and positioned at an upper portion of the housing. The closure member is configured to operate between an open position and a closed position. The closure member is operated between the open position and the closed position by manually applying force on the closure member thereby causing the closure member to be pushed down by a distance within the housing. The closure member pressed down within the housing collectively operates a hinge mechanism and a cam and lever mechanism, thereby configuring the closure member to operate between the open position and the closed position. More specifically, a second spring member of the hinge mechanism is configured to exert mechanical energy on the closure member upon releasing manual force exerted on the closure member, thereby configuring the closure member to operate between the open position and the closed position. Further, the hinge mechanism includes a regulating element that is operatively coupled to the second spring member. The regulating element is configured to control spring strength of the second spring member while operating the closure member to the open and closed positions.

The cam and lever mechanism is secured to the sidewall (e.g., the first sidewall) and positioned proximate to a proximal portion of the housing. The cam and lever mechanism is operatively coupled to the closure member. The cam and lever mechanism includes a first cam, a lever operatively coupled with the first cam and a rod secured within the housing, and a cam follower operatively coupled to the first cam. The cam follower is configured to block the movement of the first cam and the closure member when the closure member is pushed down by a distance within the housing, while configuring the closure member to operate between the open position and the closed position. In the open position, the first cam disengages with the lever thus causing the lever to rotate. The rotation of the lever enables the rod to traverse towards a distal portion of the housing to unlock a rotary mechanism. In the closed position, the first cam engages with the lever that is aligned due to movement of the rod towards the proximal portion while locking the rotary mechanism.

The rotary mechanism is secured to the first sidewall and positioned proximate to the distal portion of the housing. The rotary mechanism is operatively coupled to the drawer and configured to lock and unlock the drawer while the drawer is operated between the retracted position, the intermediate position and the extended position. The rotary mechanism includes a second cam including a third spring member, a ratchet and a fourth spring member. The second cam is operatively coupled to a latching member of the drawer. The ratchet is operatively coupled to the second cam and the rod. The fourth spring member is configured to control rotation of the ratchet while releasing the second cam and engaging with the second cam. The ratchet disengages with the second cam due to movement of the rod towards the distal portion, thereby facilitating the second cam to rotate due to force exerted by the third spring member. The rotation of the second cam disengages the latching member, thereby causing the drawer to assume the intermediate position from the retracted position. Upon disengaging the latching member, the first spring member expends the stored mechanical energy on the rear portion of the drawer which causes the drawer to be ejected out of the housing (i.e. to the intermediate position). Further, the latching member tangentially pushes the second cam while configuring the drawer to the retracted position from at least the extended position and the intermediate position. This enables the second cam to rotate until it engages with the ratchet, thus resulting in locking of the latching member. In this scenario, the first spring member stores the mechanical energy while configuring the drawer to assume the retracted position from at least the intermediate position and the extended position. Further, engaging the second cam with the ratchet facilitates the rod to move towards the proximal portion which aligns the lever for engaging with the first cam when the closure member is operated in the closed position.

The sterilizing apparatus further includes a plurality of ultraviolet (UV) lights mounted within the housing. The plurality of UV lights is configured to emit UV radiation for a pre-determined time for sterilizing the input devices resting on the drawer. One or more sensors are communicably coupled to the closure member and the drawer. The one or more sensors are configured to detect and track the movement of the closure member operating in the open position and the closed position and the movement of the drawer operating in the retracted position, the intermediate position and the extended position. A timer circuit is communicably coupled to the one or more sensors. The timer circuit activates the plurality of UV lights for the pre-determined time to sterilize the input devices based on receiving sensory signals from the one or more sensors related to the drawer and the closure member operated in the retracted position and the closed position respectively. In addition, inner surfaces of the housing, a bottom surface of the closure member and the drawer include a reflective material. The reflective material is configured to redistribute the UV radiation emitted from the plurality of UV lights onto the input devices.

Various embodiments of a sterilizing apparatus for input devices of computers are described with reference to FIGS. 1A and 1B to FIGS. 5A and 5B.

Figure 1B:
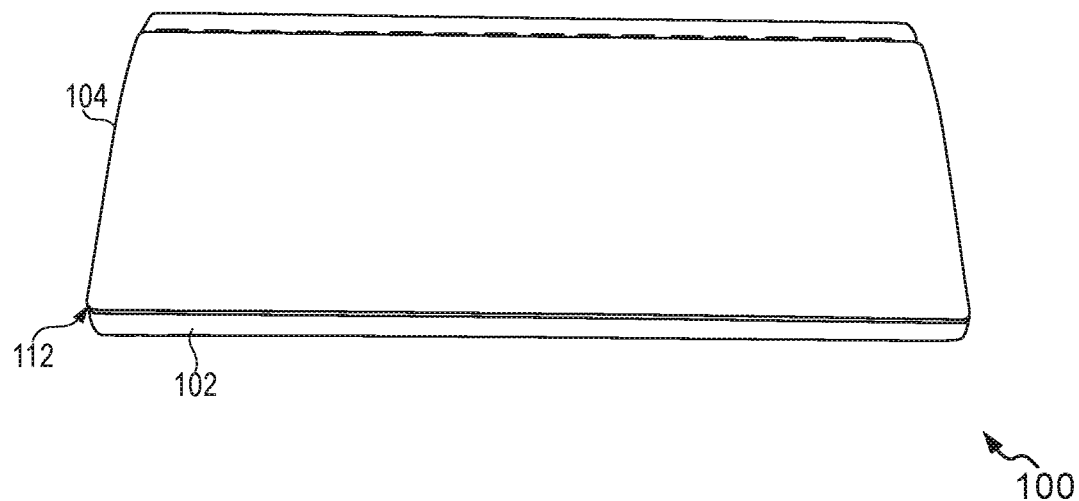
FIG. 1B illustrates a schematic view of the sterilizing apparatus operated in a closed position, in accordance with an example embodiment of the present disclosure.

FIGS. 1A and 1B illustrate a schematic view of a sterilizing apparatus 100, in accordance with an example embodiment of the present disclosure. The sterilizing apparatus 100 is configured to sterilize input devices (see, 108 of FIG. 1A) after each use. Particularly, the sterilizing apparatus 100 is configured to kill germs including bacteria and viruses present on surfaces of the input devices 108 by using ultraviolet (UV) radiation (hereinafter interchangeably referred to as "UV-C light") emitted by a UV light source mounted within the sterilizing apparatus 100, thus, preventing transmission of micro-organisms or germs from one user to another after every usage.

As shown in FIG. 1A, the sterilizing apparatus 100 includes a housing 102. The housing 102 is designed to encase the input devices 108 of a computer, such as a keyboard and a mouse resting on a drawer 110. The housing 102 may also be designed and dimensioned to encase other devices such as touch pad or a lap-top, a Tablet PC, a monitor and the like. Therefore, the input devices 108 depicted in FIG. 1A should not be taken to limit the scope of the present disclosure. The sterilizing apparatus 100 includes a closure member 104 movably coupled to the housing 102 and located at an upper portion 102a of the housing 102. In an embodiment, the closure member 104 may be an integral component of the housing 102. The closure member 104 may be implemented as a lid. Additionally, or alternatively, the closure member 104 can be implemented as a door, a cover or any other suitable movable component as per the design feasibility and requirement. The closure member 104 is configured to operate between an open position (see, 106 of FIG. 1A) and a closed position (see, 112 of FIG. 1B). More specifically, the closure member 104 is manually operated by a user for configuring the closure member 104 to assume the open position 106 and the closed position 112. Operating the closure member 104 to the closed position 112 and the open position 106 is further explained in detail. In an embodiment, the sterilizing apparatus 100 may include a motor and at least one sensor (e.g., proximity sensor or touchless sensor) operatively coupled to the closure member 104, which allows the user to operate the closure member 104 automatically between the closed position 112 and the open position 106.

The closure member 104 may be configured with the dimensions in conformity with the dimensions of the housing 102, such that the closure member 104 completely seals the housing 102 when operated in the closed position 112 (e.g., as shown in FIG. 1B). Further, inner surfaces (see, 226 of FIG. 2A) of the housing 102 define an enclosure for the input devices 108 resting on the drawer 110 and contained within the housing 102, when the closure member 104 is operated in the closed position 112. The drawer 110 is ejected from within the housing 102 when the closure member 104 is operated in the open position 106 (e.g., as shown in FIG. 1A). The drawer 110 is ejected from within the housing 102 by a spring-loaded mechanism which is further explained in detail. The drawer 110 ejected from within the housing 102 when the closure member 104 is operated in the open position, partially exposes the input devices 108 supported on the drawer 110 (e.g., as shown in FIG. 1A).

The housing 102 may be made of materials or a combination of materials that are designed to prevent or block transmission of UV radiation emitted inside the housing 102 to outside environment while sanitizing the input devices 108. Examples of the materials for fabricating the housing 102 are glass, metal (e.g., tin or aluminum), polycarbonate, carbon black and the like. Similarly, the closure member 104 is made of materials that are configured to block transmission of the UV radiation to outer surroundings, while sanitizing the input devices 108. Additionally, the housing 102 and the closure member 104 may be made of materials that are designed to block the UV radiation of a specific UV wavelength. For example, the UV-C light may have a UV wavelength of range 100-280 nanometers, thus suitable materials may be selected for fabricating the housing 102 and the closure member 104 for blocking the transmission of the UV-C light of wavelength ranging from 100-280 nanometers. Similarly, the housing 102 and the closure member 104 may be fabricated with suitable materials or combination of materials that are configured to block UV-B light of wavelength ranging from 280-315 nanometers and UV-A light of wavelength ranging from 315-400 nanometers. Preventing the transmission of the UV-C light results in sterilization of the input devices 108 in an efficient manner. Further, preventing transmission of the UV radiation protects the user and the outer environment, as exposure to the UV radiation may lead to chronic health disease for the user and cause harmful effects to the outer environment. In an embodiment, the housing 102 or the closure member 104 or both may be configured to be transparent or translucent. In such configurations, the user may notice adequate visible light during the sterilizing process through the translucent closure member 104 and/or the housing 102.

Figure 2A:
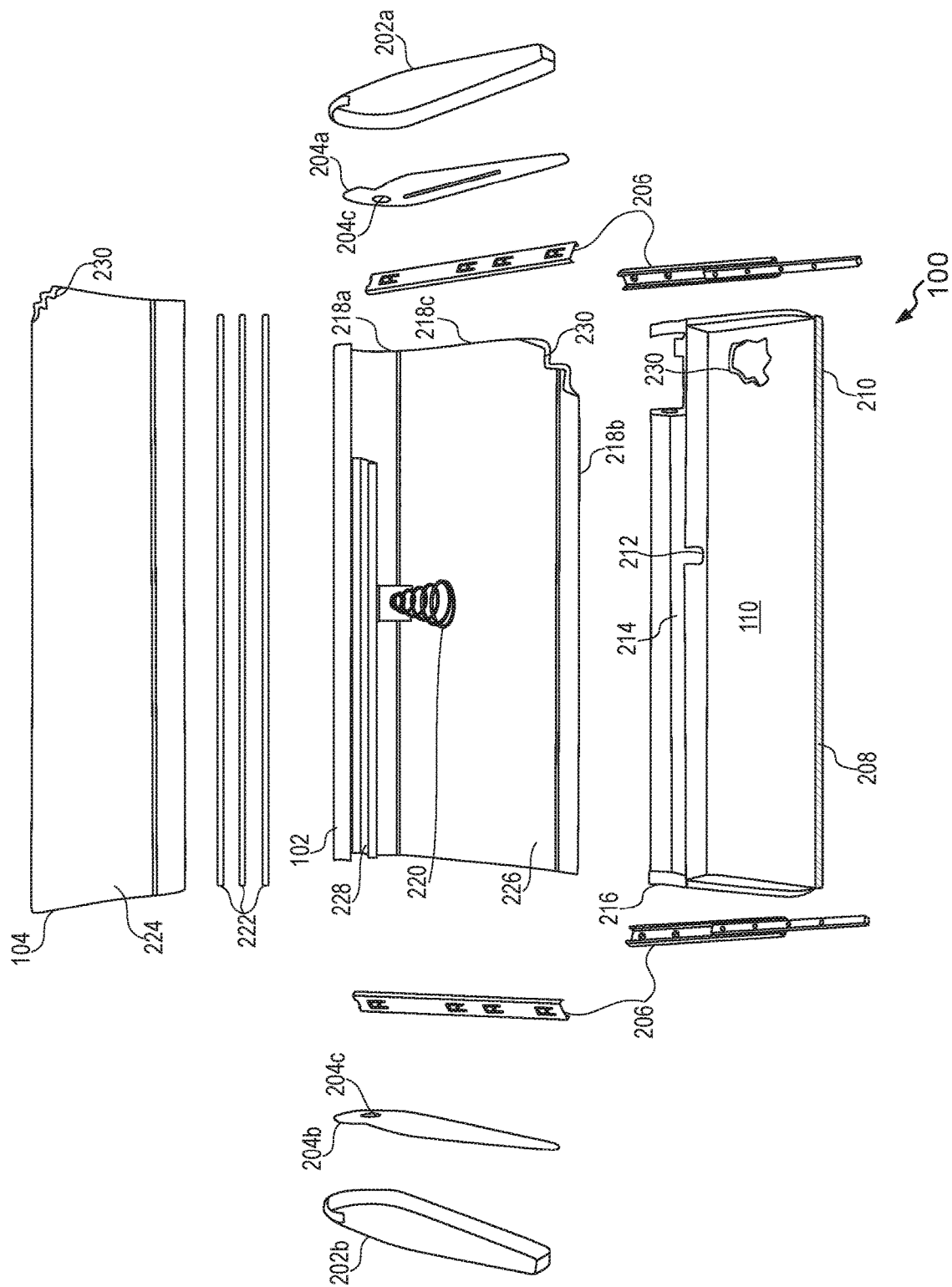
FIG. 2A illustrates an exploded view of the sterilizing apparatus, in accordance with an example embodiment of the present disclosure.

Referring to FIG. 2A in conjunction with FIGS. 1A and 1B, an exploded view of the sterilizing apparatus 100, depicting one or more components associated with the sterilizing apparatus 100 is illustrated. The sterilizing apparatus 100 includes the housing 102, the closure member 104 and the drawer 110 which are described above. Further, the housing 102 includes a first side support 202a and a second side support 202b. The first and second side supports 202a and 202b may be affixed to the housing 102. The first and second side supports 202a and 202b affixed to the housing 102 conform to a unibody construction. Alternatively, the first and second side supports 202a and 202b may be detachably mounted to the housing 102.

The housing 102 further includes at least a first sidewall 204a and a second sidewall 204b. The first and second sidewalls 204a and 204b are positioned proximate to the first and second side supports 202a and 202b respectively. The first and second sidewalls 204a and 204b positioned proximate to the first and second side supports 202a and 202b define a passageway (see, 234 of FIG. 2B) therebetween. The first and second sidewalls 204a and 204b support mounting of guiderails 206. Further, at least the first and second sidewalls 204a and 204b support mounting of a locking and unlocking mechanism for the closure member 104 and the drawer 110 which is explained further in detail. The drawer 110 is slidably secured to the housing 102 via the guiderails 206. More specifically, the guiderails 206 are mounted to a surface of each of the first and second sidewalls 204a and 204b that are oriented towards an interior portion of the housing 102. The guiderails 206 mounted to the first and second sidewalls 204a and 204b are slidably coupled to the drawer 110.

Figure 2B:
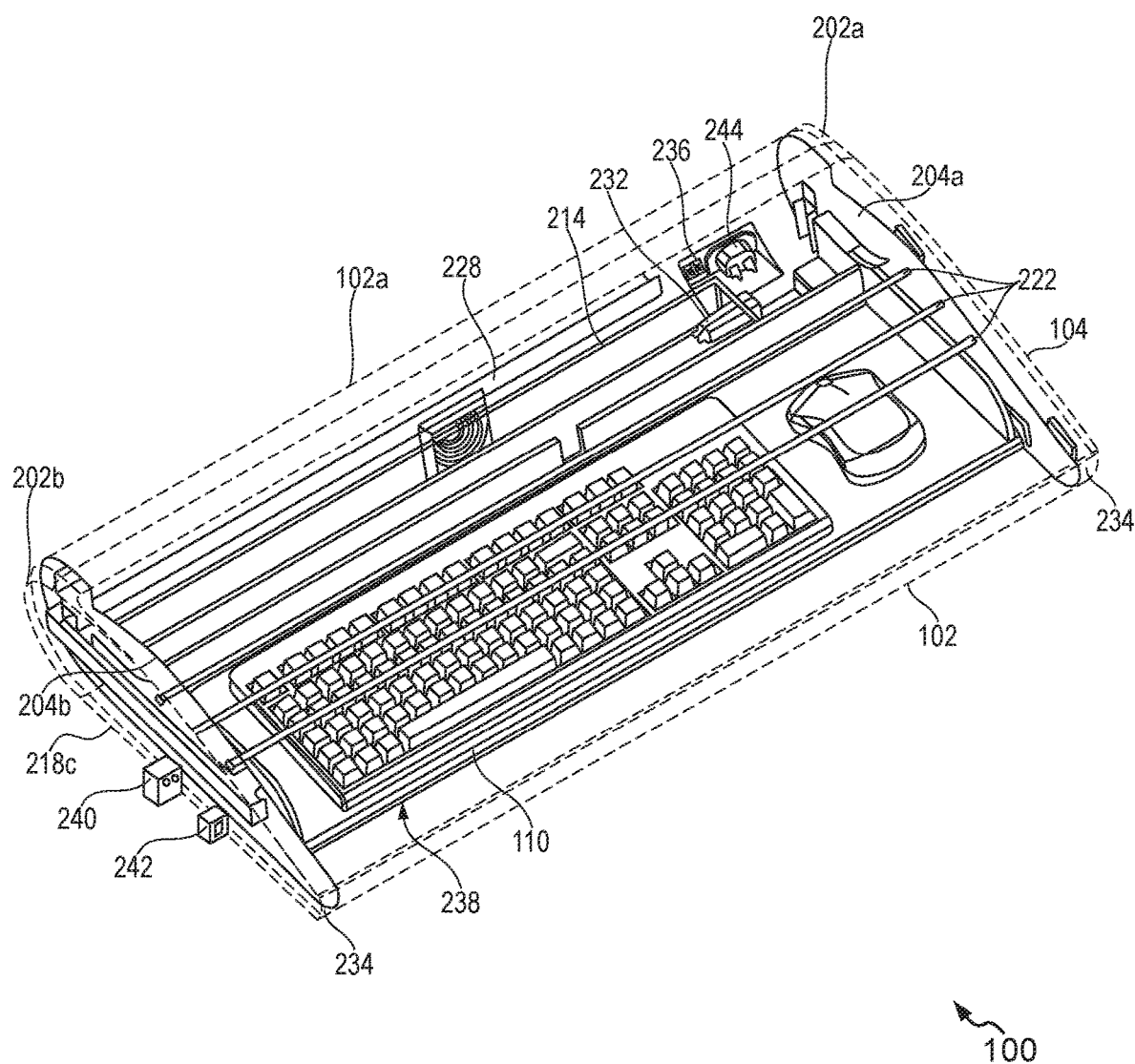
FIG. 2B is a left perspective view of the sterilizing apparatus, in accordance with an example embodiment of the present disclosure.

The drawer 110 may be designed suitably to support the input devices 108 that are to be sterilized after every usage. In general, the drawer 110 may be a flat shelf for accommodating the input devices 108 for UV sterilization. In an embodiment, the drawer 110 may include separate compartments for receiving the corresponding input devices 108 (i.e. the keyboard and the mouse). The drawer 110 slidably secured to the housing 102 may be configured to traverse along a length of the guiderails 206 for assuming a retracted position (see, 238 of FIG. 2B), an intermediate position (see, 402 of FIG. 4C) and an extended position (see, 404 of FIG. 4D). In other words, the guiderails 206 allow the drawer 110 to be substantially translated from within the housing 102 (i.e. the retracted position 238) to outside of the housing 102 (i.e. the intermediate position 402 and the extended position 404). The drawer 110 may be operated either manually or automatically for configuring the drawer 110 to achieve the aforementioned positions. In an embodiment, the drawer 110 may be driven by a motor (not shown in FIGS.) between the retracted position 238, the intermediate position 402 and the extended position 404. In the retracted position 238, the input devices 108 resting on the drawer 110 are contained within the housing 102 (e.g., as shown in FIG. 2B). In the intermediate position 402, the input devices 108 resting on the drawer 110 are partially exposed outside the housing 102 (e.g., as shown in FIG. 1A). In the extended position 404, the input devices 108 resting on the drawer 110 are fully exposed for providing access to the user. Thus, the drawer 110 may be designed ergonomically for holding the input devices 108 in place, while configuring the drawer 110 to operate between the retracted position 238, the intermediate position 402 and the extended position 404. Further, the drawer 110 may include a handle 208 located at a front portion 210 of the drawer 110. The handle 208 may provide access to the user for configuring the drawer 110 to the retracted position 238, the intermediate position 402 and the extended position 404. The drawer 110 operating in the retracted position 238, the intermediate position 402 and the extended position 404 is further explained in detail.

The drawer 110 includes an opening 212 and a channel 214 configured proximate to a rear portion 216 of the drawer 110. The opening 212 is configured to allow connectors (not shown in FIGS.) of the respective input devices 108 to pass through and enter the channel 214. The connectors (e.g., universal serial bus (USB) interface cables) of the input devices 108 entering from the opening 212 may be accommodated in the channel 214. The drawer 110 includes two or more internal USB ports (see, 232 of FIG. 2B) mounted to the channel 214. Each of the internal USB ports 232 is configured to receive connectors of the respective input devices 108 passing through the opening 212 and laid out in the channel 214.

The sterilizing apparatus 100 includes a first spring member 220 mounted within the housing 102. In particular, the first spring member 220 is mounted to a distal portion 218a of the housing 102. The first spring member 220 may be a conical or a tapered compression spring (e.g., as shown in FIGS. 2A), such that a small diameter portion of the spring is mounted to the distal portion 218a and a larger diameter portion of the spring is operatively engaged with the rear portion 216 of the drawer 110. The first spring member 220 is configured to expend mechanical energy on the rear portion 216 of the drawer 110, thereby configuring the drawer 110 to assume the intermediate position 402 from the retracted position 238 which is further explained in detail.

The location of the first spring member 220 mounted within the housing 102 may be selected such that the force exerted by the first spring member 220 is utilized maximum for operating the drawer 110 between the retracted position 238 and the intermediate position 402. Further, the force exerted on the rear portion 216 for configuring the drawer 110 to assume the intermediate position 402 from the retracted position 238 depends on number of turnings and wire diameter between each turning. Alternatively, the first spring member 220 may be selected from a group, including but not limited to, a cylindrical compression spring, a leaf spring, a mold spring and a pressure spring as per the design feasibility and requirements.

The sterilizing apparatus 100 includes a plurality of UV lights 222 mounted within the housing 102. More specifically, each of the UV lights 222 is extending between the first and second sidewalls 204a and 204b and positioned underneath a bottom surface 224 of the closure member 104 when the closure member 104 is operated in the closed position 112 (e.g., as shown in FIG. 2B). In other words, the UV lights 222 mounted within the housing 102 are juxtaposed above the input devices 108, when the drawer 110 supporting the input devices 108 is operated in the retracted position 238 (i.e. contained within the housing 102). In an embodiment, the UV lights 222 may be mounted to any other suitable locations within the housing 102 as per the design feasibility and requirement. In another embodiment, the UV lights 222 may be mounted to the bottom surface 224 of the closure member 104. For the purpose of illustration, only three UV lights are mounted within the housing 102 for sterilizing the input devices 108 and they can be in any other number depending upon the design feasibility and requirement. In one implementation, the UV lights 222 may be selected based on the number of input devices to be sterilized. Further, if additional UV lights are used, the UV radiation of a greater range may be directed onto the input devices 108, thereby resulting in reduction of the operating time of the UV lights 222 for sterilizing the input devices 108.

The UV lights 222 may be configured to emit UV radiation of wavelength ranging from 100 nanometers to 280 nanometers. The UV-C light ranging from 100 nanometers to 280 nanometers possesses germicidal effect, thus optimizing the sterilization of the input devices 108. In other words, the UV radiation of the above mentioned wavelengths is configured to inhibit replication of microorganism's DNA and renders the microorganism harmless. In one configuration, the UV-C light of range 100 nanometers to 280 nanometers may be emitted through multiple light emitting diodes (LEDs). In another configuration, the UV-C light of the specified wavelengths may be emitted by using a low pressure mercury-vapor UV bulbs or any other type of bulbs as per the design feasibility and requirements.

The UV lights 222 extending between the first and second sidewalls 204a and 204b are electrically connected to a power receiving port (see, 244 of FIG. 2B). The power receiving port 244 may be mounted to the distal portion 218a of the housing 102 and located proximate to the first sidewall 204a (e.g., as shown in FIG. 2B). The power receiving port 244 may be configured to provide power supply to the UV lights 222 and one or more circuitry components may be associated with the sterilizing apparatus 100 received from an external power source (not shown in FIGS.). The power supply from the power receiving port 244 may be transmitted to the UV lights 222 via electrical cables (not shown in FIGS.) laid out within the housing 102. The cables/wires can include a USB interface cable, a FireWire cable, and/or may just be 2 USB interface cables, USB C cable, Thunderbolt or any other serial or parallel interface cables. The electrical cables may be laid out in the passageway 234 at a left side of the housing 102 and traverse along a cabinet member (see, 228 of FIG. 2A) mounted proximate to the upper portion 102a and may further enter into the passageway 234 at a right side of the housing 102. The cables enter to the cabinet member 228 from the left side of the housing 102 and may pass into the right side of the housing 102 via an aperture 204c configured on each of the first and second sidewalls 204a and 204b. The cables laid out in the housing 102 enables the electrical connection between the UV lights 222 and the power receiving port 224. It should be noted that the cables may enter from the left side of the housing 102 to the right side of the housing 102 for electrically connecting the UV lights as described above. Thus, channeling of the cables for electrically connecting the UV lights 222 does not interrupt at least the closure member 104 and the drawer 110, while operating in the open position 106 and the closed position 112, and the retracted position 238, the intermediate position 402 and the extended position 404 respectively. In an embodiment, the housing 102 may include one or more circuitry components such as, but not limited to, resistors, diodes, and microprocessors. The one or more circuitry components may be configured for conditioning and filtering the input electrical power to deliver optimum power supply to the UV lights 222 for sterilizing.

Further, the housing 102 includes at least one external USB ports 236 mounted to the distal portion 218a. The external USB ports 236 are configured to receive connectors from corresponding input/output ports of external computing devices such as, a central processing unit (CPU), a Laptop and the like, thus enabling connection with the input devices 108. In one implementation, the external USB ports 236 may be configured to receive power supply via the external computing devices and transmit the power supply to the UV lights 222 and the one or more circuitry components associated with the sterilizing apparatus 100. In another implementation, the sterilizing apparatus 100 may include, but not limited to, a battery, a capacitor and the like for providing power supply to the UV lights 222 as per the requirements.

The UV lights 222 are configured to emit UV-C light for a pre-determined time interval to sterilize the input devices 108 resting on the drawer 110. Further, the UV lights 222 are activated for sterilizing the input devices 108 when the drawer 110 and the closure member 104 are operated in the retracted position 238 and the closed position 112 respectively. More specifically, the sterilizing apparatus 100 includes one or more sensors 240 (hereinafter referred to as "sensors 240") mounted at suitable location of the housing 102 (exemplary depicted to be on an outer surface of the second side support 202b). In one configuration, the sensors 240 may be mounted within the housing 102 such that it does not hinder the movement of at least the closure member 104 and the drawer 110. The sensors 240 are communicably coupled to the closure member 104 and the drawer 110. The sensors 240 may be a motion sensor such as a microwave motion sensor, an infrared motion sensor and the like. The sensors 240 may be configured to detect and track the movement of the closure member operating in the closed position 112 and the open position 106. Similarly, the sensors 240 may be configured to detect and track the movement of the drawer 110 operating in the retracted position 238, the intermediate position 402 and the extended position 404. Further, the sterilizing apparatus 100 includes a timer circuit 242 mounted at a suitable location of the housing 102 (exemplary depicted to be on the outer surface of the second side support 202b). Alternatively, the timer circuit 242 may be mounted within the housing 102 or at any other suitable locations of the housing 102 as per the design feasibility. The timer circuit 242 is communicably coupled to the sensors 240 and configured to activate the UV lights 222 based on the sensory signals received from the sensors 240 which is further explained in detail.

In addition, the inner surfaces 226 of the housing 102, the bottom surface 224 of the closure member 104 and the drawer 110 may include reflective material 230. For the purposes of illustration, a portion of the housing 102, the closure member 104 and the drawer 110 are bisected angularly at one corner in FIG. 2A for enabling visualization of the reflective material 230. For example, the reflective material 230 may be a mylar film, aluminum and the like. The reflective material 230 may be coated onto the inner surfaces 226, the bottom surface 224 and the drawer 110. Alternatively, the reflective material 230 may be secured to the inner surfaces 226, the bottom surface 224 and the drawer 110 by using adhesives or any other suitable means as per the design feasibility and requirement. The reflective material 230 is configured to redistribute or direct the UV-C light emitted from the UV lights 222 onto the input devices 108 from different angles. To that effect, the reflective material 230 effectuates the sterilizing of the input devices 108. The reflective material 230 causes reduction in operating time of the UV lights 222 for sterilizing the input devices 108. In an embodiment, the input devices 108 may be made of translucent materials, thereby resulting in maximum exposure of surfaces of the input devices 108 to the UV-C light.

Figure 3A:
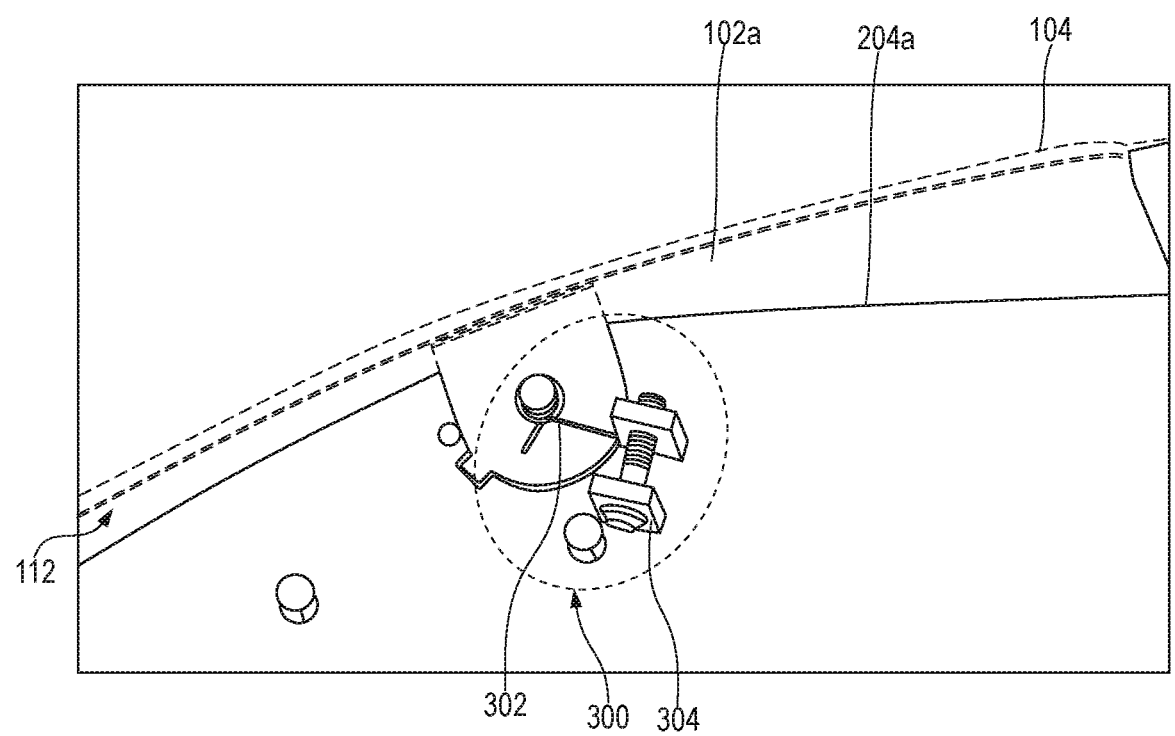
FIG. 3A is a sectional view of a portion of the sterilizing apparatus, depicting a hinge mechanism when a closure member is operated in the closed position, in accordance with an example embodiment of the present disclosure.

Referring now to FIG. 3A, the sterilizing apparatus 100 includes a hinge mechanism 300 mounted to the first sidewall 204a and located proximate to the upper portion 102a of the housing 102. The hinge mechanism 300 is operatively coupled to the closure member 104. The hinge mechanism 300 includes a second spring member 302. The second spring member 302 may be a torsion spring such that one end of the torsion spring is attached to the closure member 104 and the other end is attached to the first sidewall 204a via a regulating element 304. The second spring member 302 is configured to store mechanical energy when the closure member 104 is manually pressed down within the housing 102, while configuring the closure member 104 to operate between the closed position 112 and the open position 106. The stored mechanical energy enables the second spring member 302 to exert a torque in opposite direction, proportional to the amount it is twisted, thereby configuring the closure member 104 to the open position 106 from the closed position 112. The operation of the second spring member 302 while storing and exerting the mechanical energy may be regulated by the regulating element 304. The regulating element 304 may be configured to exert sufficient tension force to regulate the spring strength of the second spring member 302 while operating the closure member 104 between the open position 106 and the closed position 112. Alternatively, the second spring member 302 may be any other spring element that serves the purpose as explained above.

Figure 3B:
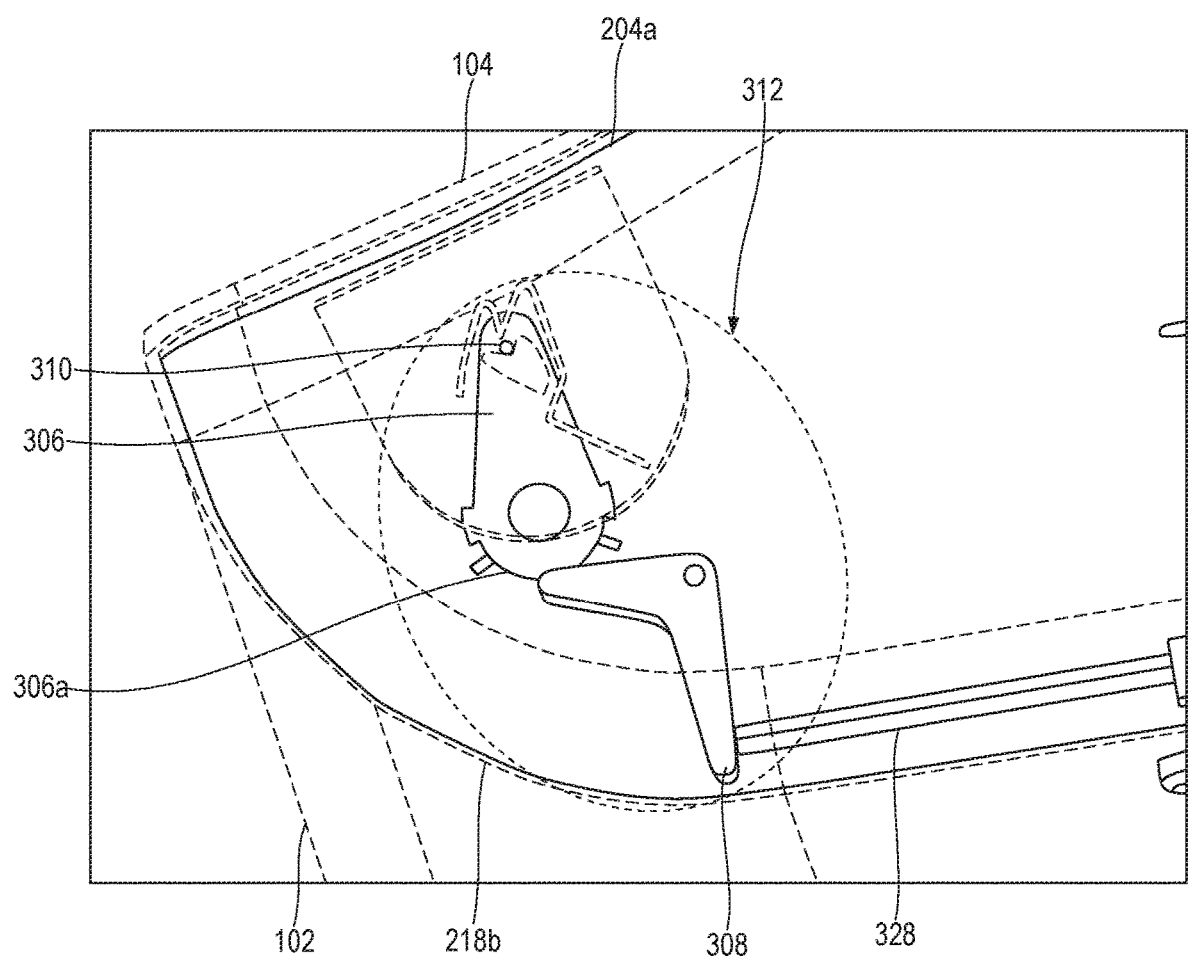
FIG. 3B is the sectional view of a portion of the sterilizing apparatus, depicting a cam and lever mechanism when the closure member is operated in the closed position, in accordance with an example embodiment of the present disclosure.

Referring now to FIG. 3B, the sterilizing apparatus 100 includes a cam and lever mechanism 312 mounted to the first sidewall 204a and located proximate to a proximal portion 218b of the housing 102. The cam and lever mechanism 312 mounted to the first sidewall 204a is operatively coupled to the closure member 104. The cam and lever mechanism 312 corresponds to an opening and closing mechanism for the closure member 104. The cam and lever mechanism 312 includes a first cam 306 mounted to the first sidewall 204a. The first cam 306 is operatively coupled with a lever 308. More specifically, a base 306a of the first cam 306 engages with the lever 308. The cam and lever mechanism 312 further includes a cam follower 310. The cam follower 310 is operatively coupled to the first cam 306. The cam follower 310 is configured to control a movement of the first cam 306 and the lever 308 while configuring the closure member 104 to operate between the closed position 112 and the open position 106.

In addition, the cam and lever mechanism 312 is operatively engaged with a rotary mechanism (see, 326 of FIG. 3C) via a rod 328. The rod 328 is mounted in the passageway 234 via support blocks and located proximate to a bottom portion (see, 218c of FIGS. 2A and 2B) of the housing 102. The rod 328 is operatively coupled to the lever 308 of the cam and lever mechanism 312 and the rotary mechanism 326. The rod 328 is configured to transmit the movement of the lever 308 to the rotary mechanism 326 while configuring the closure member 104 to the open position 106 from the closed position 112. Further, the rod 328 transmits the movement of the rotary mechanism 326 to the cam and lever mechanism 312 while configuring the drawer 110 to the retracted position 238 from the intermediate position 402.

Figure 3C:
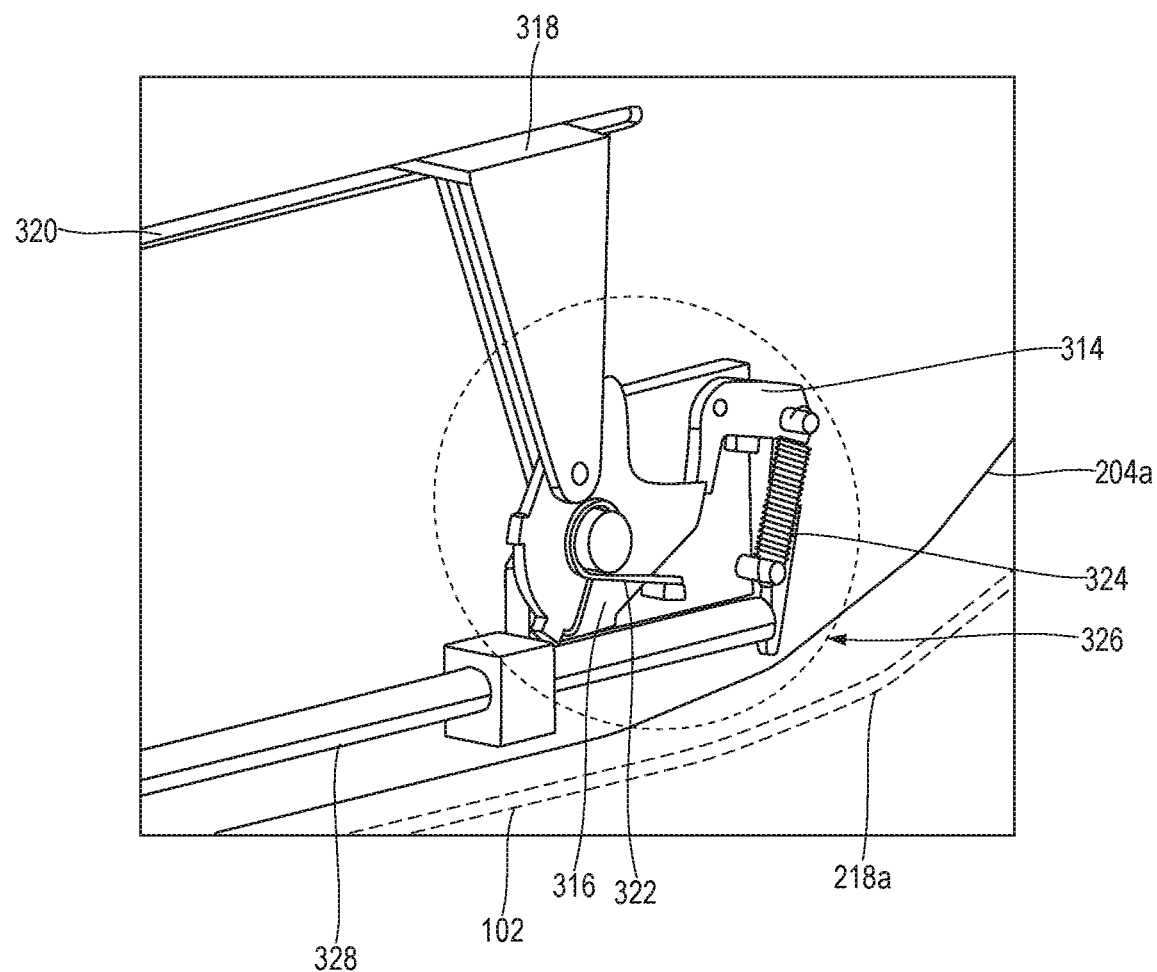
FIG. 3C is the sectional view of a portion of the sterilizing apparatus, depicting a rotary mechanism when the closure member is operated in the closed position, in accordance with an example embodiment of the present disclosure.

Referring now to FIG. 3C, the rotary mechanism 326 is mounted to the first sidewall 204a and located proximate to the distal portion 218a of the housing 102. The rotary mechanism 326 mounted to the first sidewall 204a is operatively coupled to the cam and lever mechanism 312 via the rod 328 as described above. The rotary mechanism 326 corresponds to a locking and unlocking mechanism for the drawer 110. In other words, the rotary mechanism 326 is configured to lock and unlock the drawer 110, thereby configuring the drawer 110 to assume the retracted position 238, the intermediate position 402 and the extended position 404.

The rotary mechanism 326 includes a ratchet 314. The ratchet 314 is configured to rotate based on the movement induced by the rod 328 which is explained further in detail. The ratchet 314 is operatively coupled to a second cam 316 of the rotary mechanism 326. The second cam 316 is configured to engage with a latching member 318 of the drawer 110. Particularly, the first sidewall 204a may be configured with a slit 320 extending between the rotary mechanism 326 and the cam and lever mechanism 312. In this configuration, the latching member 318 is operatively coupled to the second cam 316 via the slit 320. Further, the slit 320 enables the latching member 318 to traverse along its length while configuring the drawer 110 to operate between the retracted position 238, the intermediate position 402 and the extended position 404.

The second cam 316 includes a third spring member 322. The third spring member 322 may be a torsion spring. The third spring member 322 is configured to store and expend mechanical energy for enabling the second cam 316 to rotate. The structural configuration and functionality of the third spring member 322 is similar to that of the second spring member 302, therefore it is not described herein in detail. Alternatively, the third spring member 322 may be any other spring which serves the purpose.

The ratchet 314 includes a fourth spring member 324. The fourth spring member 324 may be a tension spring, such that one end of the tension spring is attached to the ratchet 314 and the other end of the tension spring is attached to the first sidewall 204a. The fourth spring member 324 is configured to maintain the position of the ratchet 314 while configuring the drawer 110 to assume the retracted position 238, the intermediate position 402 and the extended position 404. In other words, the fourth spring member 324 is configured to control rotation of the ratchet 314 for releasing the second cam 316 while engaging with the second cam 316. Alternatively, the fourth spring member 324 may be any other spring which serves the purpose.

FIGS. 4A-4D illustrate a stepwise articulation of each of the above mentioned mechanisms (i.e. the hinge mechanism 300, the cam and lever mechanism 312 and the rotary mechanism 326) for configuring the closure member 104 and the drawer 110 to the open position 106 from the closed position 112, and to the extended position 404 from the retracted position 238 respectively.

Figure 4A:
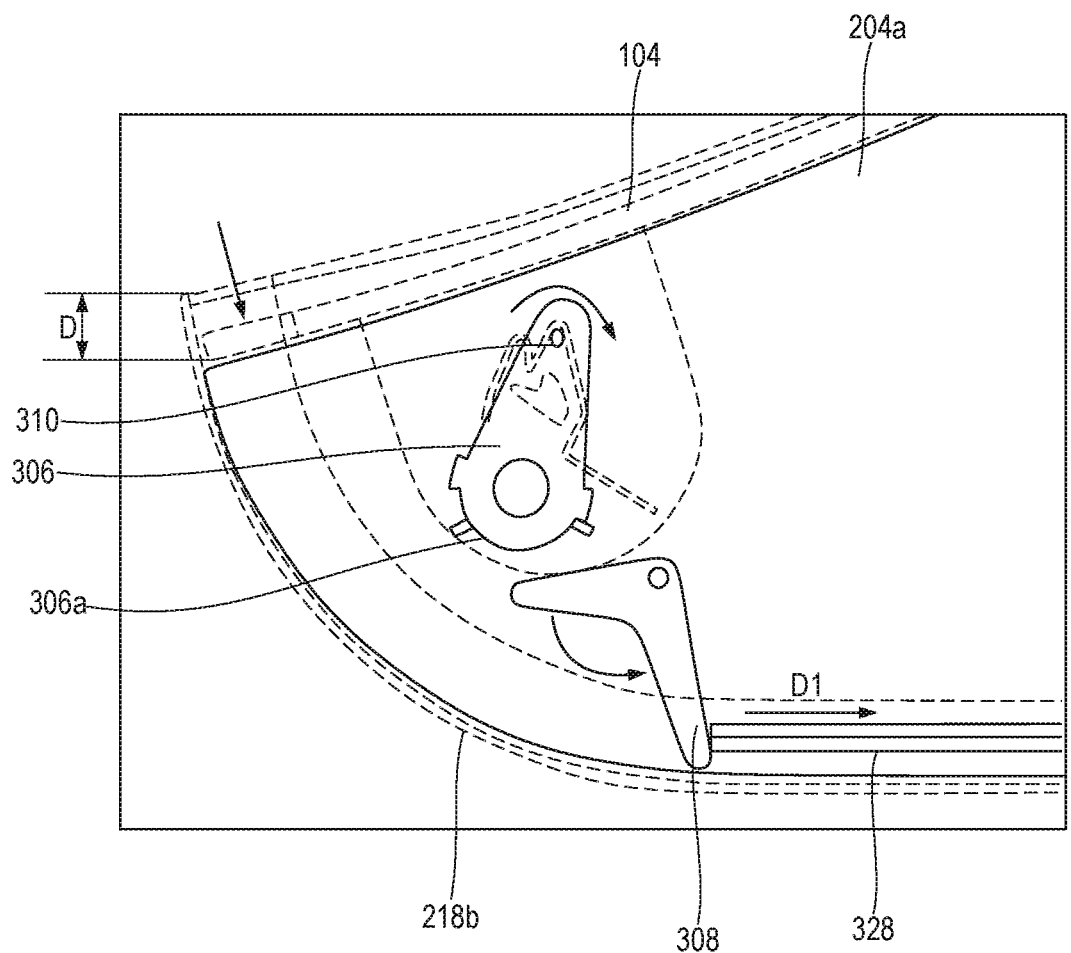
FIGS. 4A-4D illustrate a stepwise articulation of the hinge mechanism, the cam and lever mechanism and the rotary mechanism for configuring the closure member to an open position from the closed position, and a drawer to an extended position from a retracted position, in accordance with an example embodiment of the present disclosure.

The closure member 104 is manually pushed down by a distance 'D' within the housing 102 (e.g., as shown in FIG. 4A). In other words, the user may apply force on a top surface 104a of the closure member 104, thus causing the closure member 104 to be pushed down by the distance 'D' within the housing 102. The closure member 104 pushed down within the housing 102 enables twisting of the second spring member 302, thus resulting in storing of the mechanical energy. Upon releasing the manual force applied onto the top surface 104a, the second spring member 302 exerts the force or torque in the opposite direction. The torque exerted by the second spring member 302 is proportional to the distance 'D' to which the closure member 104 is pushed down within the housing 102. The torque exerted by the second spring member 302 forces up the closure member 104 to the open position 106 from the closed position 112 (e.g., as shown in FIG. 4C). For example, the closure member 104 operated in the open position 106 may be positioned at 3 inches above the drawer 110. The distance (i.e. 3 inches) to which the closure member 104 is operated in the open position 106 may be controlled by the regulating element 304 of the hinge mechanism 300.

Referring to FIG. 4A, the closure member 104 pushed down within the housing 102 enables the first cam 306 to disengage with the lever 308 and rotate in a clockwise direction. The cam follower 310 is configured to lock the closure member 104 when it is pushed down within the housing 102, thus restricting the movement of the closure member 104 beyond the distance 'D'. Consequently, the rotation of the first cam 306 is also controlled by the cam follower 310 when the closure member 104 is pushed down within the housing 102. It should be noted that the rotation of the first cam 306 depends on the distance 'D' to which the closure member 104 is pushed down within the housing 102. Further, the rotation of the first cam 306 upon disengaging with the lever 308 enables the lever 308 to rotate in a direction opposite to that of the rotation of the first cam 306. More specifically, the base 306a of the first cam 306 pushes the lever 308 during initial movement of the first cam 306, thus configuring the lever 308 to rotate in an anticlockwise direction. The rotation of the lever 308 enables the rod 328 to move towards the distal portion 218a. The direction of movement of the rod 328 towards the distal portion 218a is depicted with a directional arrow 'D1'. The rod 328 moving towards the distal portion 218a transmits the movement of the lever 308 to the rotary mechanism 326 as explained above.

Figure 4B:
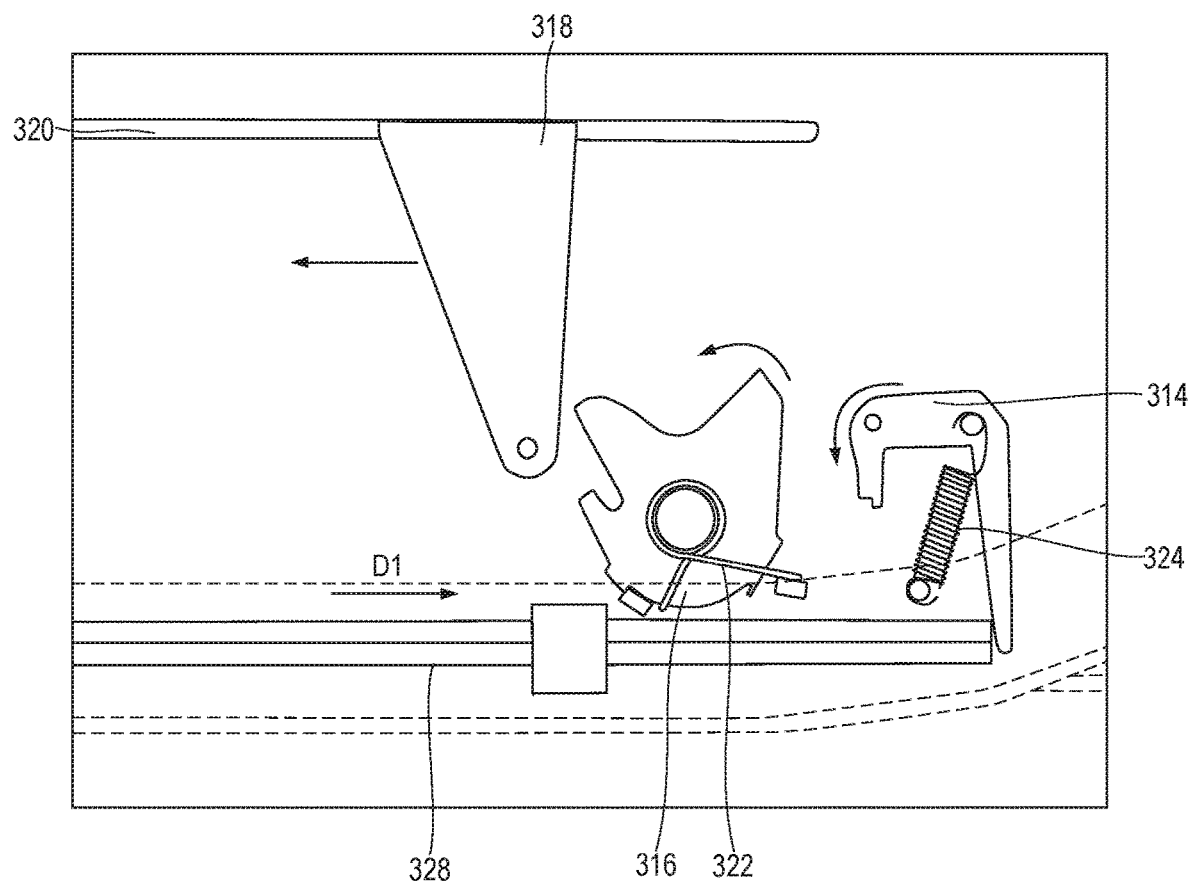
Figure 4C:
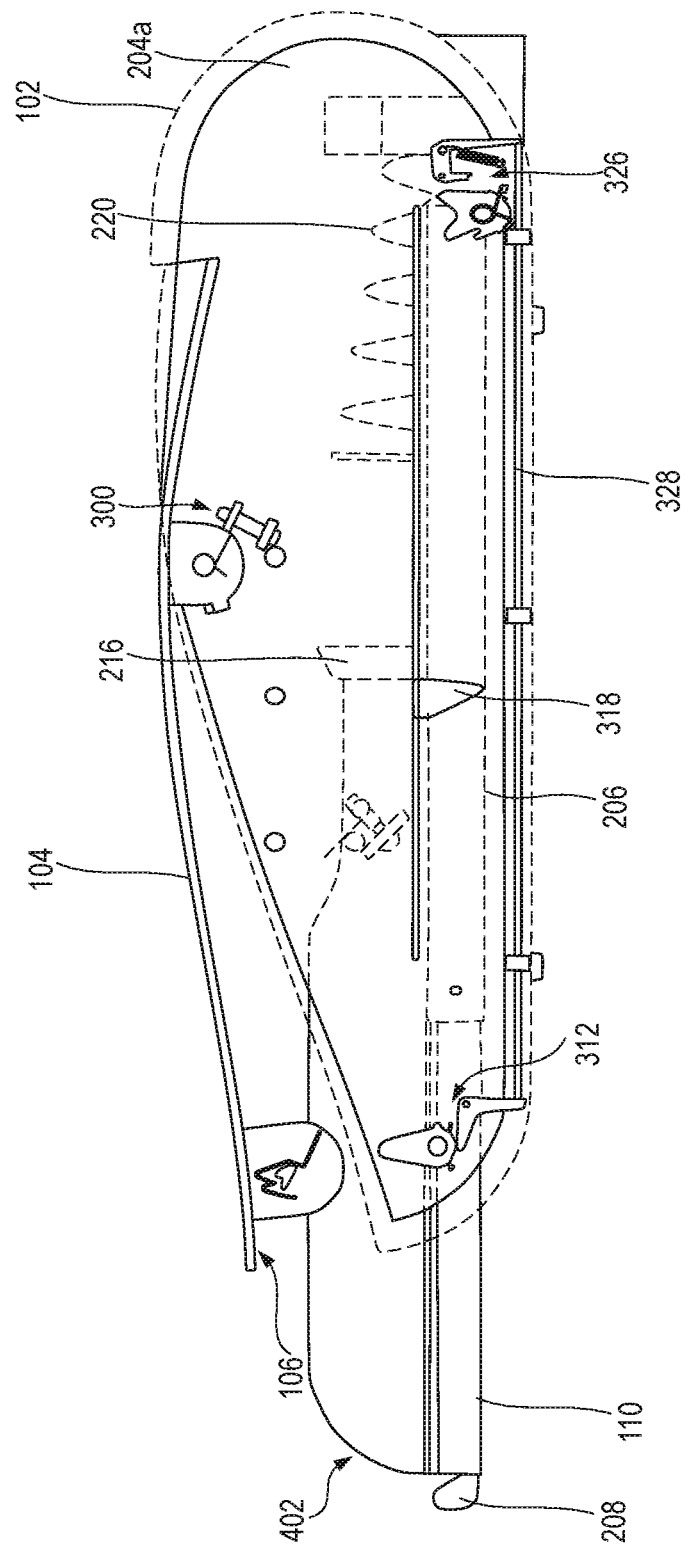

Referring now to FIG. 4B, the rod 328 moving towards the distal portion 218a pushes the ratchet 314, thus enabling the ratchet 314 to rotate in the anticlockwise direction. The rotation of the ratchet 314 disengages the second cam 316. Upon disengaging with the ratchet 314, the ratchet 314 is maintained in position by the fourth spring member 324. More specifically, the fourth spring member 324 controls the rotation of the ratchet 314 upon disengaging with the second cam 316, in order to maintain the position of the rod 328 moved towards the distal portion 218a due to the movement of the lever 308.

Upon disengaging with the ratchet 314, the second cam 316 rotates in the anticlockwise direction due to force exerted by the third spring member 322. Further, the rotation of the second cam 316 disengages the latching member 318 of the drawer 110, thus unlocking the drawer 110. The third spring member 322 maintains the position of the second cam 316 for engaging with the latching member 318 while configuring the drawer 110 to the retracted position 238 from at least the intermediate position 402 and the extended position 404.

Figure 4D:
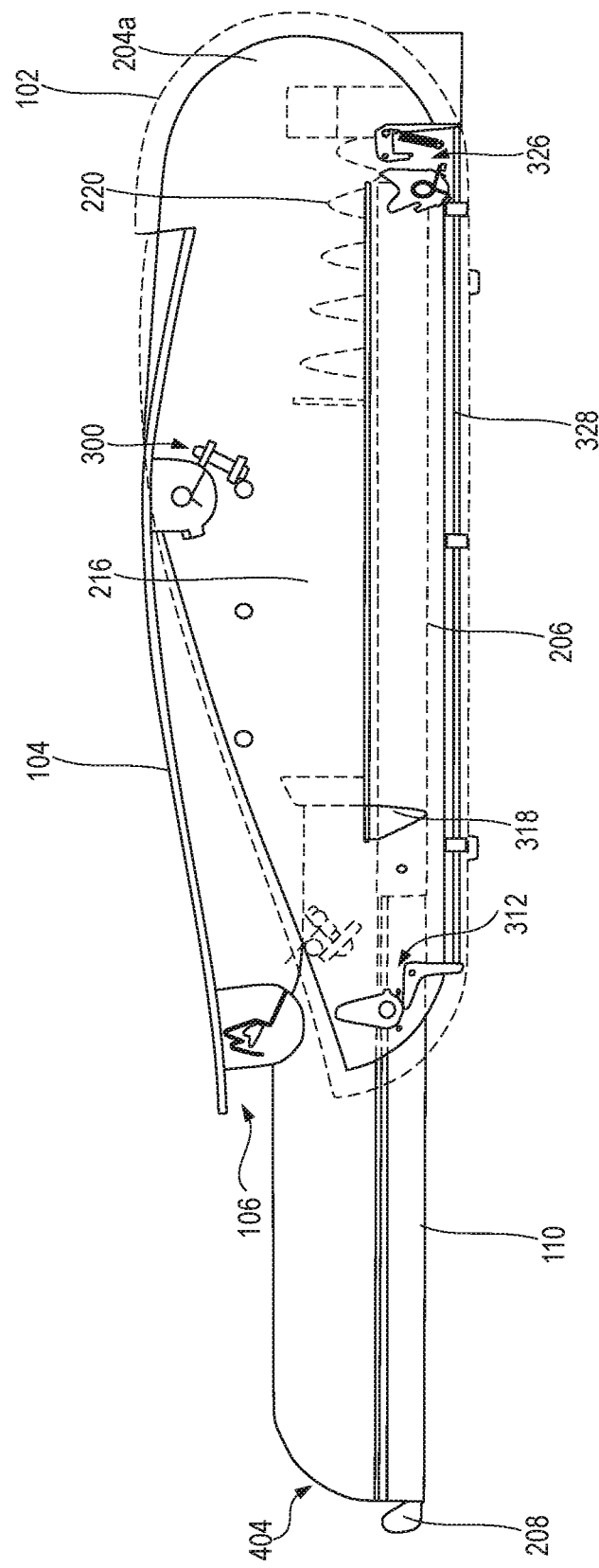

As the latching member 318 disengages with the second cam 316, the drawer 110 is configured to assume the intermediate position 402 from the retracted position 238 (e.g., as shown in FIG. 4C). More specifically, the drawer 110 is pushed towards the intermediate position 402 when the latching member 318 disengages from the second cam 316 due to the force exerted by the first spring member 220 on the rear portion 216 of the drawer 110. It should be noted that the first spring member 220 is operated to an expanded state when the drawer 110 is operated in an intermediate position 402 (e.g., as shown in FIG. 4C). The drawer 110 operated in the intermediate position 402 partially exposes the input devices 108 resting on the drawer 110. For example, the drawer 110 may come up to 3 inches out of the housing 102 when the drawer 110 is operated in the intermediate position 402. Further, the drawer 110 operated in the intermediate position 402 provides access to the handle 208 (e.g., as shown in FIG. 4C). The user may access the handle 208 for manually operating the drawer 110 to the extended position 404 from the intermediate position 402 (e.g., as shown in FIG. 4D). The drawer 110 operated in the extended position 404 provides access to the input devices 108 for the user.

Figure 5A:
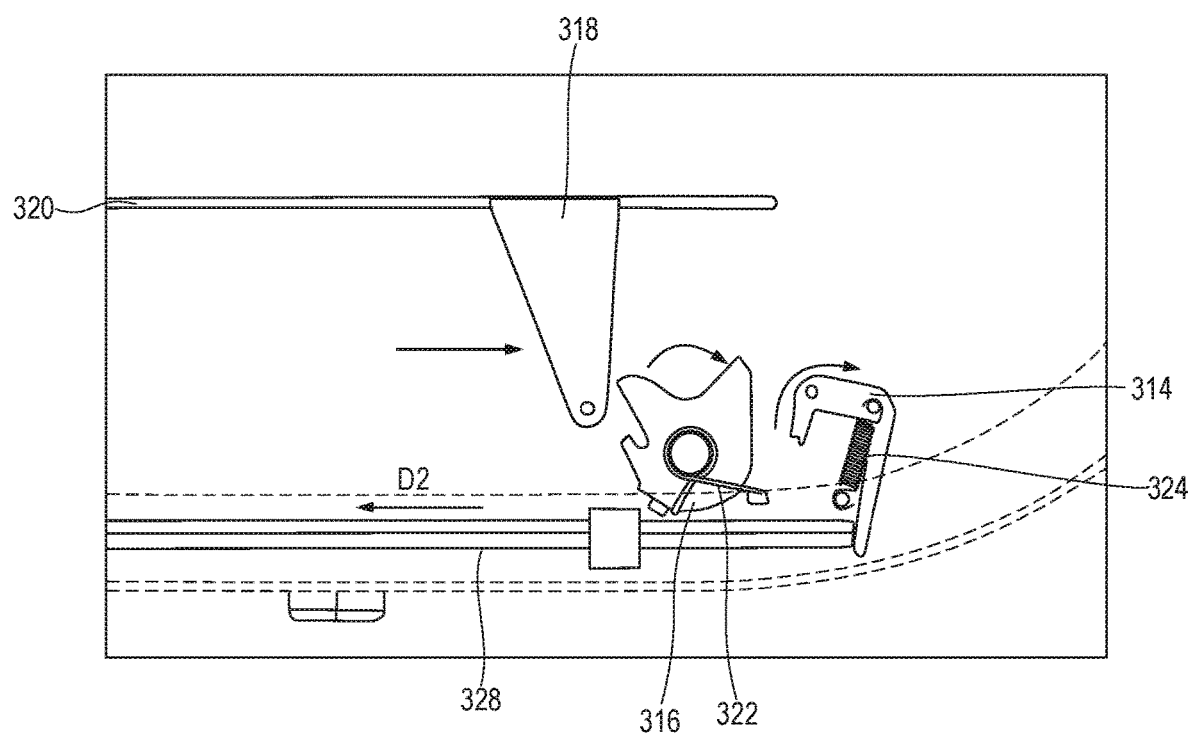
FIGS. 5A and 5B illustrate the stepwise articulation of the hinge mechanism, the cam and lever mechanism and the rotary mechanism for configuring the closure member to the closed position from the open position, and the drawer to the retracted position from the extended position, in accordance with an example embodiment of the present disclosure.
Figure 5B:
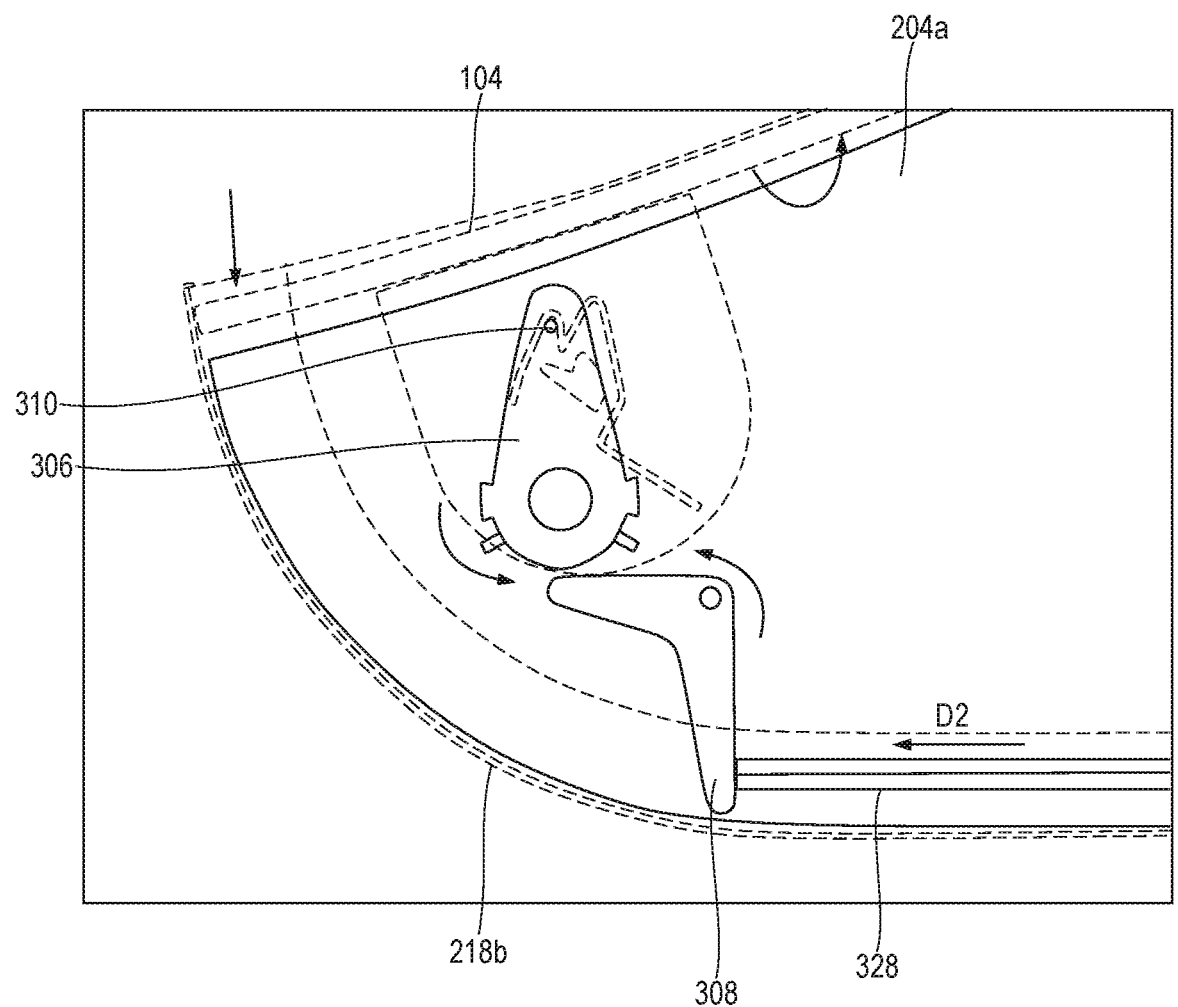

FIGS. 5A and 5B illustrate the stepwise articulation of each of the above mentioned mechanisms (i.e. the hinge mechanism 300, the cam and lever mechanism 312 and the rotary mechanism 326) for configuring the closure member 104 and the drawer 110 to the closed position 112 from the open position 106, and to the retracted position 238 from at least the intermediate position 402 and the extended position 404 respectively.

Referring now to FIG. 5A, the drawer 110 is manually pushed within the housing 102 (i.e. the retracted position 238), prior to operating the closure member 104 to the closed position 112. The user may access the handle 208 for pushing the drawer 110 from at least the extended position 404 and the intermediate position 402 to the retracted position 238. The drawer 110 being manually pushed inside the housing 102 enables the latching member 318 to traverse towards the distal portion 218a. Thus, the latching member 318 moving towards the distal portion 218a tangentially pushes the second cam 316, thus enabling the second cam 316 to rotate (i.e. in clockwise direction) until it engages with the ratchet 314 (e.g., as shown in FIG. 3C). Engaging the second cam 316 with the ratchet 314 enables the second cam 316 to block the movement of the latching member 318, thereby resulting in locking of the drawer 110 (e.g., as shown in FIG. 3C). It should be noted that the latching member 318 locks to the second cam 316 when the drawer 110 attains the retracted position 238. The rotation of the second cam 316 while engaging with the ratchet 314, activates the first spring member 220, the third spring member 322 and the fourth spring member 324 to store the mechanical energy. Further, the third spring member 322 and the fourth spring member 324 maintains the position of the second cam 316 when the second cam 316 is engaged with the ratchet 314, thus preventing collapse of the second cam 316 and the ratchet 314 which may enable the drawer 110 to be operated in the intermediate position 402.

The second cam 316 engaging with the ratchet 314 enables the ratchet 314 to rotate in the clockwise direction. The rotation of the ratchet 314 induces movement to the rod 328, thus enabling the rod 328 to traverse towards the proximal portion 218b of the housing 102. The direction of movement of the rod 328 towards the proximal portion 218b is depicted with a directional arrow 'D2'. The rod 328 moving towards the proximal portion 218b aligns the lever 308 (e.g., as shown in FIG. 3B) for engaging with the first cam 306 while configuring the closure member 104 to the closed position 112 from the open position 106.

Referring now to FIG. 5B, the first cam 306 is configured to rotate in the anticlockwise direction when the closure member 104 is pushed down within the housing 102 while configuring the closure member 104 to the closed position 112 from the open position 106. The cam follower 310 locks the first cam 306 and the closure member 104 which enables the first cam 306 to engage with the lever 308 (e.g., as shown in FIG. 3B) while operating the closure member 104 to the closed position 112. In this scenario, the closure member 104 when pushed down within the housing 102 enables the second spring member 302 to store the mechanical energy as explained above. The second spring member 302 exerts torque in the opposite direction which forces up the closure member 104 (e.g., as shown in FIG. 5B), thereby configuring the closure member 104 to the closed position 112 (e.g., as shown in FIG. 1B).

Referring back to FIG. 2B, the sensors 240 communicably coupled to the closure member 104 and the drawer 110 are configured to detect and track the movement of the closure member 104 and the drawer 110 as explained above. Further, the timer circuit 242 is configured to activate the UV lights 222 based on receiving the sensory signals from the sensors 240 related to the closure member 104 operated in the closed position 112 and the drawer 110 operated in the retracted position 238. The timer circuit 242 is configured to activate the UV lights 222 for the pre-determined time (e.g., 2-10 minutes). The UV lights 222 emit UV-C light for the pre-determined time for sanitizing the germs or microorganisms present on the input devices 108. As such, the activation time of the UV lights 222 may be programmed or provided by a control logic based on the wavelength range of the UV-C light emitted by the UV lights 222, thus resulting in sanitization of the input devices 108 in an efficient manner. In one implementation, the timer circuit 242 may be programmed to keep the UV lights 222 turned 'ON' until the closure member 104 is operated in the open position 106. In an embodiment, the sterilizing apparatus 100 may include an interface (not shown in FIGS.) for receiving inputs related to the activation time from the user.

Further, the timer circuit 242 communicably coupled with sensors 240 may be configured to shut off the UV lights 222 based on detecting movement of the closure member 104. For instance, the user may push the closure member 104 for configuring it to operate in the open position 106. In such scenarios, the physical movement of the closure member 104 is detected by the sensors 240 and transmits the sensory signals related to the physical movement of the closure member 104 to the timer circuit 242. The timer circuit 242 shuts off or deactivates the UV lights 222 just before the initial movement of the closure member 104 transitioning from the closed position 112 to the open position 106, thus, deactivating the UV lights 222 before transitioning of the closure member 104 to the open position 106 prevents transmission of UV radiation to outside of the housing 102.

In one embodiment, the sterilizing apparatus 100 may include one or more status indicators (not shown in Figures). The status indicators may be configured to indicate the status of the closure member 104 operated in the closed position 112 and various conditions associated with the sterilizing apparatus 100. The status indicators may also indicate the status of sterilizing process. For example, the status indicators may indicate the user when the sterilization of the input devices 108 is completed and indicate when the sterilization process is interrupted when the closure member 104 is operated to the open position 106 during the sterilizing process.

Various embodiments of the disclosure, as discussed above, may be practiced with steps and/or operations in a different order, and/or with hardware elements in configurations, which are different than those which, are disclosed. Therefore, although the disclosure has been described based upon these exemplary embodiments, it is noted that certain modifications, variations, and alternative constructions may be apparent and well within the spirit and scope of the disclosure.

Although various exemplary embodiments of the disclosure are described herein in a language specific to structural features and/or methodological acts, the subject matter defined in the appended claims is not necessarily limited to the specific features or acts described above. Rather, the specific features and acts described above are disclosed as exemplary forms of implementing the claims.

What is claimed is:

1. A sterilization apparatus, comprising:
   a housing at least comprising a first sidewall and a second sidewall;
   a drawer slidably secured to the housing via guide rails mounted to the first and second sidewalls, the drawer adapted to receive input devices, the drawer configured to operate between a retracted position, an intermediate position and an extended position;
   a rotary mechanism secured to the first sidewall and positioned proximate to a distal portion of the housing, the rotary mechanism operatively coupled to the drawer, the rotary mechanism configured to lock and unlock the drawer, thereby operating the drawer between the retracted position, the intermediate position and the extended position;
   a plurality of ultraviolet (UV) lights mounted within the housing, the plurality of UV lights configured to emit UV radiation for a pre-determined time for sterilizing the input devices resting on the drawer;
   a closure member movably coupled to the housing and positioned at an upper portion of the housing, the closure member configured to operate between an open position and a closed position;
   a cam and lever mechanism secured to the first sidewall and positioned proximate to a proximal portion of the housing, the cam and lever mechanism operatively coupled to the closure member; and
   a hinge mechanism secured to the first sidewall and operatively coupled to the closure member, the hinge mechanism configured to operate the closure member between the open position and the closed position,
      wherein the closure member is operated between the open position and the closed position by manually applying force on the closure member, thereby causing the closure member to be pushed down by a distance within the housing, wherein pushing down of the closure member within the housing collectively operates the hinge mechanism and the cam and lever mechanism, thereby configuring the closure member to operate between the open position and the closed position.

2. The sterilization apparatus as claimed in claim 1, wherein the drawer assumes the intermediate position from the retracted position using a first spring member mounted within the housing and located at the distal portion of the housing, and the first spring member is configured to store mechanical energy while configuring the drawer to assume the retracted position from at least the intermediate position and the extended position and expend the stored mechanical energy on a rear portion of the drawer.

3. The sterilization apparatus as claimed in claim 1, wherein the hinge mechanism during the operation between the open position and the closed position exerts mechanical energy on the closure member upon releasing a manual force exerted on the closure member using a second spring member and wherein the second spring member is operatively coupled to a regulating element, the regulating element is configured to control spring strength of the second spring member while operating the closure member to the open position and the closed position.

4. The sterilization apparatus as claimed in claim 1 while configuring the closure member to operate between the open position and the closed position, the cam and lever mechanism are configured to operate:
a first cam;
a lever operatively coupled with the first cam and a rod secured within the housing; and a cam follower operatively coupled to the first cam,
wherein the cam follower is configured to block movement of the first cam and the closure member when the closure member is pushed down by the distance within the housing.

5. The sterilization apparatus as claimed in claim 4, wherein the closure member is configured to assume the open position and the closed position when the closure member is pushed down by the distance inside the housing, such that:
in the open position, the first cam disengages with the lever, thus causing the lever to rotate, wherein the rotation of the lever enables the rod to traverse towards the distal portion to unlock the rotary mechanism, and
in the closed position, the first cam engages with the lever that is aligned due to movement of the rod towards the proximal portion while locking the rotary mechanism.

6. The sterilization apparatus as claimed in claim 1, wherein the rotary mechanism during the operation of at least the intermediate position, the retracted position and the extended position is configured to operate:
a second cam including a third spring member, the second cam operatively coupled to a latching member of the drawer;
a ratchet operatively coupled to the second cam and a rod secured within the housing; and
a fourth spring member configured to control rotation of the ratchet for releasing the second cam while engaging with the second cam,
wherein the rotation of the second cam upon disengaging from the ratchet configures the drawer to assume the intermediate position from the retracted position and the rotation of the second cam while engaging with the ratchet configures the drawer to assume the retracted position from at least the intermediate position and the extended position.

7. The sterilization apparatus as claimed in claim 6, wherein the ratchet disengages with the second cam due to movement of the rod towards the distal portion, thereby facilitating the second cam to rotate due to force exerted by the third spring member, wherein the rotation of the second cam disengages the latching member from the second cam, thereby causing the drawer to assume the intermediate position from the retracted position.

8. The sterilization apparatus as claimed in claim 6, wherein the latching member tangentially pushes the second cam while configuring the drawer to the retracted position from at least the extended position and the intermediate position, thus enabling the second cam to rotate until it engages with the ratchet, wherein engaging the second cam with the ratchet facilitates the rod to move towards the proximal portion which aligns a lever for engaging with a first cam of the cam and lever mechanism.

9. The sterilization apparatus as claimed in claim 1, further comprising:
one or more sensors communicably coupled to the closure member and the drawer, the one or more sensors configured to detect and track movement of the closure member operating in the open position and the closed position and movement of the drawer operating in the retracted position, the intermediate position and the extended position; and
a timer circuit communicably coupled to the one or more sensors, wherein the timer circuit activates the plurality of UV lights for the pre-determined time to sterilize the input devices based on receiving sensory signals from the one or more sensors related to the drawer and the closure member operated in the retracted position and the closed position respectively.

10. The sterilization apparatus as claimed in claim 1, wherein inner surfaces of the housing, a bottom surface of the closure member and the drawer comprise a reflective material, the reflective material configured to redistribute the UV radiation emitted from the plurality of UV lights onto the input devices.

11. The sterilization apparatus as claimed in claim 1, wherein the drawer comprises a handle located at a front portion of the drawer, wherein the handle provides access to a user for manually operating the drawer to the extended position from the intermediate position, thereby providing access to the input devices to the user, and to the retracted position from at least the extended position and the intermediate position for encasing the input devices resting on the drawer within the housing.

12. A sterilization apparatus for input devices, the sterilization apparatus comprising: a housing at least comprising a first sidewall and a second sidewall;
a drawer slidably secured to the housing via guide rails mounted to the first and second sidewalls, the drawer adapted to receive the input devices, the drawer configured to operate between a retracted position, an intermediate position and an extended position;
a rotary mechanism secured to the first sidewall and positioned proximate to a distal portion of the housing, the rotary mechanism operatively coupled to the drawer, the rotary mechanism configured to lock and unlock the drawer, thereby operating the drawer between the retracted position, the intermediate position and the extended position;

a plurality of ultraviolet (UV) lights mounted within the housing, the plurality of UV lights configured to emit UV radiation for a pre-determined time for sterilizing the input devices resting on the drawer;

a closure member movably coupled to the housing and positioned at an upper portion of the housing, the closure member configured to operate between an open position and a closed position;

a cam and lever mechanism secured to the first sidewall and positioned proximate to a proximal portion of the housing, the cam and lever mechanism operatively coupled to the closure member; and a hinge mechanism secured to the first sidewall and operatively coupled to the closure member, the hinge mechanism configured to operate the closure member between the open position and the closed position, wherein the closure member is operated between the open position and the closed position by manually applying force on the closure member thereby causing the closure member to be pushed down by a distance within the housing, wherein pushing down of the closure member within the housing collectively operates the hinge mechanism and the cam and lever mechanism, thereby configuring the closure member operate between the open position and the closed position;

one or more sensors communicably coupled to the closure member and the drawer, the one or more sensors configured to detect and track movement of the closure member operating in the open position and the closed position and movement of the drawer operating in the retracted position, the intermediate position and the extended position; and a timer circuit communicably coupled to the one or more sensors, wherein the timer circuit activates the plurality of UV lights for the pre-determined time to sterilize the input devices based on receiving sensory signals from the one or more sensors related to the drawer and the closure member operated in the retracted position and the closed position respectively.

13. The sterilization apparatus as claimed in claim 12, wherein the drawer assumes the intermediate position from the retracted position using a first spring member mounted within the housing and located at the distal portion of the housing, the first spring member configured to store mechanical energy while configuring the drawer to assume the retracted position from at least the intermediate position and the extended position and expend the stored mechanical energy on a rear portion of the drawer.

14. The sterilization apparatus as claimed in claim 12, wherein the hinge mechanism during the operation between the open position and the closed position
exerts mechanical energy on the closure member upon releasing a manual force exerted on the closure member a second spring member, and
wherein the second spring member is operatively coupled to a regulating element, the regulating element is configured to control spring strength of the second spring member while operating the closure member to the open position and the closed position.

15. The sterilization apparatus as claimed in claim 12, while configuring the closure member to operate between the open position and the closed position the cam and lever mechanism are configured to operate:
a first cam;
a lever operatively coupled with the first cam and a rod secured within the housing; and a cam follower operatively coupled to the first cam,
wherein the cam follower is configured to block movement of the first cam and the closure member when the closure member is pushed down by a distance within the housing.

16. The sterilization apparatus as claimed in claim 15, wherein the closure member is configured to assume the open position and the closed position when the closure member is pushed down by the distance inside the housing, such that:
in the open position, the first cam disengages with the lever thus causing the lever to rotate, wherein the rotation of the lever enables the rod to traverse towards the distal portion to unlock the rotary mechanism, and
in the closed position, the first cam engages with the lever that is aligned due to movement of the rod towards the proximal portion while locking the rotary mechanism.

17. The sterilization apparatus as claimed in claim 12, wherein the rotary mechanism during the operation of at least the intermediate position, the retracted position and the extended position is configured to operate:
a second cam including a third spring member, the second cam operatively coupled to a latching member of the drawer;
a ratchet operatively coupled to the second cam and a rod secured within the housing; and
a fourth spring member configured to control rotation of the ratchet while releasing the second cam and while engaging with the second cam,
wherein rotation of the second cam upon disengaging from the ratchet configures the drawer to assume the intermediate position from the retracted position and the rotation of the second cam while engaging with the ratchet configures the drawer to assume the retracted position from at least the intermediate position and the extended position.

18. The sterilization apparatus as claimed in claim 17, wherein the ratchet disengages with the second cam due to movement of the rod towards the distal portion, thereby facilitating the second cam to rotate due to force exerted by the third spring member, wherein the rotation of the second cam disengages the latching member from the second cam, thereby resulting the drawer to assume the intermediate position from the retracted position.

19. The sterilization apparatus as claimed in claim 17, wherein the latching member tangentially pushes the second cam while configuring the drawer to the retracted position from at least the extended position and the intermediate position, thus enabling the second cam to rotate until it engages with the ratchet, wherein engaging the second cam with the ratchet facilitates the rod to move towards the proximal portion which aligns a lever for engaging with a first cam of the cam and lever mechanism.

20. The sterilization apparatus as claimed in claim 12, wherein inner surfaces of the housing, a bottom surface of the closure member and the drawer comprise a reflective material, the reflective material configured to redistribute the UV radiation emitted from the plurality of UV lights onto the input devices.

* * * * *